United States Patent
Senda et al.

(10) Patent No.: US 9,862,921 B2
(45) Date of Patent: Jan. 9, 2018

(54) METHOD FOR DETERMINING CELL STATE AND AUTOANALYZER USING SAID METHOD

(71) Applicant: Hitachi High-Technologies Corporation, Minato-ku, Tokyo (JP)

(72) Inventors: Naoko Senda, Tokyo (JP); Yoko Inoue, Tokyo (JP); Hiroaki Nakagawa, Tokyo (JP); Akihiro Shimase, Tokyo (JP); Ryota Nakajima, Tokyo (JP); Kazumichi Imai, Tokyo (JP); Shizu Takeda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1 day.

(21) Appl. No.: 14/896,123

(22) PCT Filed: Jun. 17, 2014

(86) PCT No.: PCT/JP2014/065962
§ 371 (c)(1),
(2) Date: Dec. 4, 2015

(87) PCT Pub. No.: WO2014/208391
PCT Pub. Date: Dec. 31, 2014

(65) Prior Publication Data
US 2016/0122702 A1    May 5, 2016

(30) Foreign Application Priority Data

Jun. 24, 2013   (JP) .................................. 2013-131846

(51) Int. Cl.
| | | |
|---|---|---|
| C12M 1/34 | (2006.01) | |
| C12M 1/36 | (2006.01) | |
| G01N 33/68 | (2006.01) | |
| G01N 33/50 | (2006.01) | |

(52) U.S. Cl.
CPC ............ *C12M 41/46* (2013.01); *C12M 41/48* (2013.01); *G01N 33/5005* (2013.01); *G01N 33/6806* (2013.01); *G01N 33/6812* (2013.01)

(58) Field of Classification Search
None
See application file for complete search history.

(56) References Cited

U.S. PATENT DOCUMENTS

| | | | |
|---|---|---|---|
| 2003/0091977 A1 | 5/2003 | Leese et al. | |
| 2015/0192568 A1 | 7/2015 | Shibuya et al. | |

FOREIGN PATENT DOCUMENTS

| | | |
|---|---|---|
| JP | 2003-520047 A | 7/2003 |
| JP | 2004-215585 A | 8/2004 |
| JP | 2014-45663 A | 3/2014 |

OTHER PUBLICATIONS

Lavon et al., The proteins of bovine spermatozoa from the caput and cauda epididymidis, J. Reprod. Fert. (1971) 24, 219-232.*
Naoko Senda et al., "Amino Acid Analysis of Human Epidermal Cell Sheet Culture Supernatant", Annual Meeting of the Molecular Biology Society of Japan Program Yoshishu (Web), vol. 36, Nov. 20, 2013, with unverified English translation (two (2) pages).
International Search Report (PCT/ISA/210) issued in PCT Application No. PCT/JP2014/065962 dated Aug. 19, 2014, with English translation (four (4) pages).

* cited by examiner

*Primary Examiner* — Suzanne M Noakes
*Assistant Examiner* — Stephen Chong
(74) *Attorney, Agent, or Firm* — Crowell & Moring LLP

(57) ABSTRACT

There is provided a method for noninvasively evaluating the cell state (proliferation, multi-layering, and differentiation) of a cell sheet as a mimic tissue at the time of culturing the cell sheet. The method is characterized in that an analysis of an amino acid is conducted with the use of the culture supernatant of a cell sheet to monitor a change in the concentration of any amino acid selected from a group of 5-species of amino acids (Ile, Val, Ser, Leu, and Ala), thereby making a determination.

3 Claims, 6 Drawing Sheets

FIG. 2

| | LOT A | LOT B | LOT C |
|---|---|---|---|
| PROLIF-ERATION | GOOD<br>PROLIFERATION PROCEEDED<br>UP TO COUFLUENT IN 7 DAYS | GOOD<br>PROLIFERATION PROCEEDED<br>UP TO COUFLUENT IN 9 DAYS | POOR<br>THE CELL SHEET WAS NOT FORMED<br>BECAUSE OF POOR PROLIFERATION |
| MULTI-LAYERING | ON THE ORDER OF 3 LAYERS | ON THE ORDER OF 3 LAYERS | POOR |
| DIFFEREN-TIATION | THE BASAL LAYER,<br>THE STRATUM SPINOSUM,<br>AND THE GRANULAR LAYER | THE BASAL LAYER,<br>AND THE STRATUM SPINOSUM | IN THE BASAL LAYER ONLY |

METHOD FOR DETERMINING CELL STATE AND AUTOANALYZER USING SAID METHOD

TECHNICAL FIELD

The invention relates to a method for determining the cell state of a cell sheet, and an autoanalyzer using the same.

BACKGROUND ART

Attention has lately been focused on regeneration medicine whereby a tissue produced from a stem tissue is transplanted at a site of tissue injury, thereby implementing regeneration or functional recovery of an injured tissue or organ. It is well known that transplantation of a cell sheet, as a mimic tissue, in particular, is higher in treatment effect as compared with the case of a tissue solution in which a tissue is present as a simple substance. A human epidermal keratinocyte cell sheet is now a commercial realty, and a progress in clinical application of the cell sheet for use in treatment of severe burns and so forth has since been made. With respect to this cell sheet described as above, one of problems yet to be solved is presently establishment of a method for noninvasively evaluating the cell state of a cell sheet. The cell sheet becomes a mimic tissue via three stages including a step 1 through a step 3, after the cell sheet is disseminated with cells, described as follows. The step 1: a cell is caused to adhere to a culture surface, the step 2: the cell undergoes proliferation in a single layer throughout the culture surface to form a basal layer, and the step 3: the cell is multilayered in two layers or more, and further, each of the cells, in the two layers or higher, respectively, undergoes differentiation.

With the current state of the art, the quality of a cell sheet for use in transplantation is verified by invasive evaluation, such as observation with the use of a phase-contrast microscope during culturing, histological stain against a cell sheet for use in evaluation, produced simultaneously with the cell sheet for use in transplantation, and in the same condition as is the case with the cell sheet for use in transplantation and, and so forth. However, these methods each have a disadvantage. On one hand, the observation of a cell, using the phase-contrast microscope, is noninvasive, and can be conducted whenever necessary during the culturing, however, this observation can cope with the observation of only the surface layer of the cell sheet, but cannot evaluate a cell sheet as multilayered in the step 2 onward. Further, with respect to the evaluation by the histological stain, applied to the cell sheet for use in evaluation, it is possible to evaluate an extent of the multilayering as well as differentiation, in the step 2 onward, however, since the cell sheet is fixedly attached, this evaluation represents an invasive method, and it is therefore impossible to evaluate the cell sheet itself for use in transplantation. It can be said that establishment of a noninvasive monitoring technique capable of solving these problems will enable the cell state of a cell sheet to be directly evaluated, thereby contributing to enhancement in the quality of a regenerated tissue for use in transplantation.

A method for noninvasive cell-evaluation has thus far been described in several Patent Literature. For example, in Patent Literature 1, there has been proposed a method whereby respective cells of an embryo, an egg, a karyoplast, a stem cell, and a stem cell precursor are used as a target, and a viable force of each of the targets is determined on the basis of the concentration of an amino-acid in a medium, used as an index, thereby differentiating between a healthy embryo and an abeyant embryo. This has an object of selecting the healthy embryo to be returned to a mother body in the case of an artificial insemination. If this can be realized, it will become possible to limit the number of the embryos to be returned to the mother body to one, so that multiple pregnancy can be decreased in number. Further, in Patent Literature 2, there has been proposed a method whereby a cell sheet is used as a target, and timing of multilayering is determined on the basis of a ratio of glucose concentration in medium to ammonia concentration in medium, thereby enabling proliferation to be completed at appropriate timing.

CITATION LIST

Patent Literature

PTL 1: Japanese Unexamined Patent Application Publication (Translation of PCT Application) No. 2003-520047
PTL 2: Japanese Patent Application Laid-Open No. 2004-215585

SUMMARY OF INVENTION

Technical Problem

However, unlike a call sheet, a cell adopted as a target in Patent Literature 1 does not go through culture stages unique to the case of the call sheet. For this reason, with the method disclosed in the patent literature, it is not possible to evaluate the timing as well as the extent, with respect to proliferation, multi-layering, and differentiation, respectively, although the timing as well as the extent will be indispensable at the time of evaluating the call sheet. Further, with Patent Literature 2, the multi-layering of a cell sheet being adopted as the target thereof, the differentiation of the cell sheet cannot be evaluated with this method.

It is therefore an object of the invention to noninvasively evaluate the cell state (proliferation, multi-layering, and differentiation) of a cell sheet as a mimic tissue.

Solution to Problem (1) To that end, according to one aspect of the present invention, there is provided an autoanalyzer having an automated culture unit, and an amino acid analysis unit, the automated culture unit including a culture vessel for culturing a cell sheet, and a flow-path for transporting a medium introduced in the culture vessel to the amino acid analysis unit, and the amino acid analysis unit including a detection part for measuring the respective concentrations of predetermined amino acids contained in the medium transported from the automated culture unit, a memory part for storing the respective measured concentrations of the amino acids, and a determination part for determining the cell state of the cell sheet on the basis of a change in the concentration of at least one of the amino acids stored in a memory part. For the predetermined amino acids, 5 species of amino acids of Ile, Val, Ser, Leu, and Ala are used, and the change in the concentration of the amino acid is calculated on the basis of the respective concentration of the amino acids, as measured with time by the detection part over a plurality of times to be stored in the memory part.

Further, according to another aspect of the present invention, there is provided a method for determining a cell state of a cell sheet, whereby the cell state of a cell sheet is determined by analyzing an amino acid in a culture supernatant with the use of a group of 5 species of amino acids, consisting of Ile, Val, Ser, Leu, and Ala.

Advantageous Effects of Invention

The present invention is capable of noninvasively evaluate the cell state (proliferation, multi-layering, and differentiation) of a cell sheet as a mimic tissue.

BRIEF DESCRIPTION OF DRAWINGS

FIG. 2 is a view showing a difference in the cell state (proliferation, multi-layering, and differentiation) of a cell sheet among cell lots.

DESCRIPTION OF EMBODIMENTS

First, examples of the present invention are described below.

The present invention has been developed in view of circumstances indicated by those problems described in the foregoing in order to provide a method of determining the cell state (proliferation, multi-layering, and differentiation) of a cell sheet by conducting an analysis on an amino acid by use of the culture supernatant of a cell sheet to thereby monitor a change in the concentration of any one of 5-species amino acids (Ile, Val, Ser, Leu, and Ala). An amino acid being one of metabolites of a cell, as metabolism undergoes a change accompanying a change in the state of the cell, the metabolic expenditure of the amino acid, as well, will undergo a change depending on the formation process of a cell sheet and the cell state thereof, whereupon this change is reflected in the concentration of an amid acid in the culture supernatant.

Sampling of a culture supernatant is conducted during culturing to conduct an analysis on amino acid in the culture supernatant. For a measurement sample, use may be made of a culture supernatant preceding medium replacement at timing of the replacement, or a culture supernatant extracted at timing of other than the medium replacement if the culture supernatant is small in quantity. As a method for analyzing an amid acid in the culture supernatant, a high performance liquid chromatography (HPLC) is considered potent in terms of detection accuracy, and so forth, however, the analytical method is not limited to HPLC, and any other method including a mass spectrometry (MS) may be used if it is a method capable of quantitative determination. According to the present method, since evaluation is made by use of a medium to be discarded, monitoring can be easily executed without changing a traditional culture process. Since the concentration of an amino acid will undergo a change depending on the cell state thereof, whether or not a process of the cell state (proliferation, differentiation, and multi-layering) of a cell sheet is satisfactory can be determined by a measurement made on the concentration of the amino acid, and a variation in the concentration.

Furthermore, this method for the determination of the cell state can be automated to be further built in an automated cell culture system. In such a case, automation can be achieved if a medium-replacement port of the automated cell culture system is provided with a branch where the culture supernatant is extracted from the sample during culturing to be sent out to an amino-acid analyzer of the automated cell culture system, thereby analyzing the culture supernatant.

The above and other features of the present invention will be apparent from the following preferred examples of the invention in conjunction with the accompanying drawings.

EXAMPLE 1

There are described below both a configuration and an operation of an autoanalyzer according to Example 1 of the invention.

Figure 1:
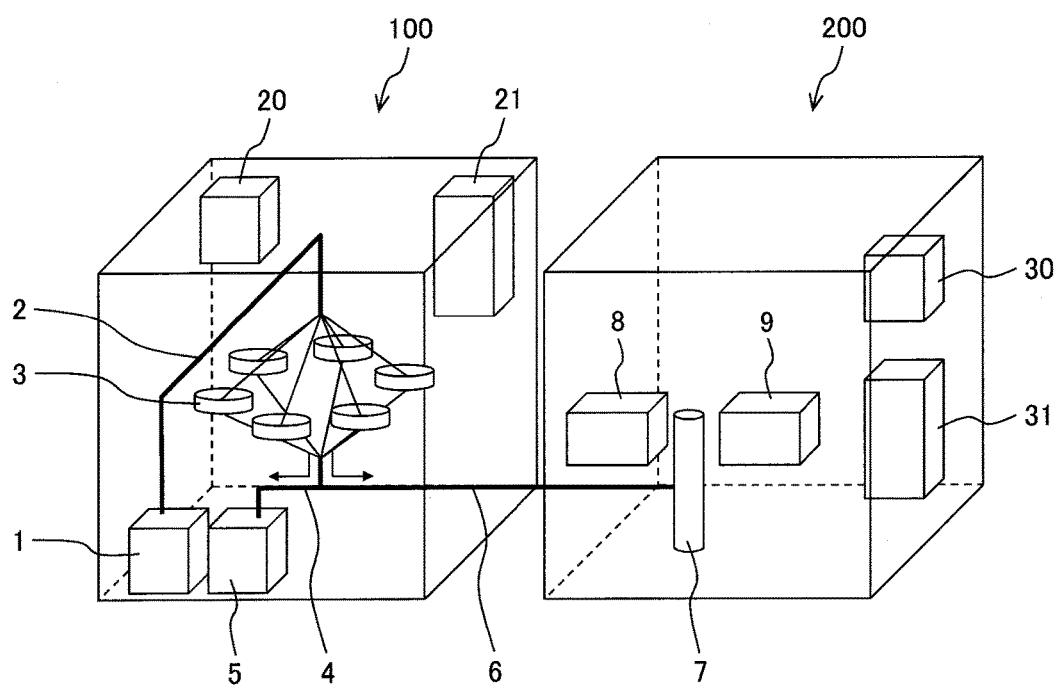
FIG. 1 is a view of an autoanalyzer incorporating analysis of amino acid in a culture supernatant.

FIG. 1 shows an autoanalyzer made up of an automated culture unit 100, and an amino acid analysis unit 200. The automated culture unit 100 incorporates a cell culture function, and the amino acid analysis unit 200 incorporates a high performance liquid chromatography (HPLC).

First, a configuration of the automated culture unit 100 is described below. The automated culture unit 100 is made up of a medium bottle 1, a medium supply flow-path 2, a culture vessel 3, an effluent flow-path 4, an effluent bottle 5, a flow-path 6 directed for culture-supernatant analysis, a temperature•humidity controller 20 and a controller 21. Normally, plural pieces of the culture vessels 3 are installed, and the effluent flow-path 4 has a bifurcation point provided in the middle thereof, the bifurcation point being provided with a control valve (not shown). The bifurcation point is changed over by the agency of the control valve to thereby cause the effluent flow-path to be connected to the effluent bottle 5 on one hand, while causing the effluent flow-path to be connected to the amino acid analysis unit 200 on the other hand. The temperature•humidity controller 20 holds both the temperature and the humidity of the automated culture unit 100, or the culture vessel 3, at respective desired values, the controller 21 controls the temperature•humidity controller 20, thereby controlling change-over of the medium to the effluent flow-path 4, or to the flow-path 6 directed for culture-supernatant analysis, and so forth. Further, wire connections for electrical connection to the temperature•humidity controller 20 and the controller 21, respectively, are omitted in FIG. 1.

Next, an operation in the automated culture unit 100 is described below.

The medium is supplied from the medium bottle 1 to the culture vessel 3 via the medium supply flow-path 2 to be subsequently used for cell culture. An old medium that will become the effluent at the time of medium replacement is sent out from the culture vessel 3 to be discarded into the effluent bottle 5 after passing through the effluent flow-path 4, however, a portion of the culture supernatant is carried to the amino acid analysis unit 200 via the flow-path 6 directed for culture-supernatant analysis, to be branched off from the effluent flow-path 4, whereupon the concentration of an amid acid in the culture supernatant is analyzed. At the time of determining the cell state on the basis of the concentration of an amid acid in the culture supernatant, use is made of a correlation between the cell state and the concentration of an amid acid in the culture supernatant, as found in advance.

Now, both the configuration and the operation of the amino acid analysis unit 200 are described below. The amino acid analysis unit 200 is made up of a high performance liquid chromatography (HPLC), a determination part 30, and a memory part 31. The HPLC is equipped with an analysis column 7, a detection part 9, and so forth. For a detector of the detection part 9, use can be made of a mass spectrometry (not shown) or a spectroscopic analyzer, and so forth. In the case of using the spectroscopic analyzer, an optical system 8 is in use. Furthermore, wire connections for electrical connection to the determination part 30, and the memory part 31, respectively, are omitted in FIG. 1.

The medium carried to the amino acid analysis unit 200 via the flow-path 6 directed for culture-supernatant analysis is introduced into the analysis column 7 inside the HPLC, and the concentration of the medium passing through the analysis column 7 is detected by the detection part 9, whereupon the concentration of the amid acid in the culture supernatant is analyzed.

The concentration of the amid acid, measured by the detection part 9, is once stored in the memory part 31. Normally, a measurement on the concentration of the amid acid is made for every medium replacements carried out at a predetermined intervals (on a day-to-day basis) after the start of culturing. The measurement on the concentration of the amino acid at a point of the medium replacement, in time, is made over a plurality of times until the completion of culturing.

The determination part 30 calculates variations in the concentration of the amino acid on the basis of data on plural concentrations of the amino acid, stored in the memory part 31. Both calculated variations and medium-replacement days are stored in the memory part 31. The determination part 30 finds time-dependent changes in the concentration of the amino acid on the basis of data on the medium-replacement days, and the variations, stored in the memory part 31.

Meanwhile, a threshold is pre-stored in the memory part 31. The threshold is to serve as a reference value for use in determining whether or not a change in the concentration of an amino acid is a variation having a significant difference.

The determination part 30 makes use of the time-dependent change in the concentration of the amino acid, the variation, and the threshold, as described above, to thereby determine whether or not the cell state of a cell sheet, that is, proliferation, multi-layering, and differentiation are satisfactorily proceeding, and whether or not a normal cell fails to grow due to an anomalous occurrence.

The autoanalyzer according to the present invention executes determination on the cell state of a cell sheet on the basis of a method for determining the cell state of a cell sheet, as described in Example 2 of the invention.

EXAMPLE 2

<<Cell Sheet Culture>>

First, there are shown below culture stages until a cell sheet as a target of the present invention is normally produced.

An epidermal cell adheres to a culture surface in around 24 hours after disseminated. The cell as adhered undergoes proliferation in a planar state up to confluent in around several days onward, whereupon a first one of layers, as formed, becomes the basal layer of the cell sheet. Thereafter, the cell undergoes proliferation in layers so as to be multi-layered, and the cells, in a second one of the layers, and above, undergo differentiation with the elapse of a few weeks, whereupon the cell becomes a cell sheet resembling a human epidermal keratinocyte cell.

Hereunder, "confluent" indicates a state in which a cell undergoes proliferation in the planar state, and the basal layer of a cell sheet is formed, as shown under (2), as above. Further, "a cell state" indicates the respective states of a cell, such as proliferation, multi-layering, and differentiation, in a cell sheet, in particular.

Now, a living-organism epidermal cell is of a layered structure made up of a basal layer, a stratum spinosum, a granular layer, and a keratinized layer, stacked in this order, starting from the bottom of the cell, and as progress is made in differentiation, in the cell sheet, formation of the stratum spinosum, the granular layer, and the keratinized layer is observed.

With a method of evaluating a cell sheet, use is commonly made of evaluation with the use of a phase-contrast microscope is commonly adopted during culturing, while commonly adopting histological stain after culturing. In observing the cell sheet, using the phase-contrast microscope, the number of cells present on a culture surface and the shape of the cell are checked. With this method, it is possible to noninvasively determine whether or not the cell proliferation is normal, however, the multi-layering as well as the differentiation of a cell sheet, at a point in time, corresponding to the middle of culturing or thereafter, or the completion of culturing, cannot be determined.

Still further, with evaluation on the histological stain of a cell sheet, a section prepared by fixing a tissue thereto is stained with hematoxylin and eosin stain or immunostaining, thereby checking the multi-layering as well as the differentiation of the cell sheet. With this method, it is possible to determine an extent of the multi-layering as well as the differentiation of a cell sheet after the completion of culturing, however, this method being invasive one because fixing of the tissue and staining are required, so that this method cannot be applied during culturing, and the cell sheet as evaluated cannot be used for transplantation.

<<Monitoring of Culture Supernatant Amino Acid at the Time of Human Epidermal Keratinocyte Cell Sheet Culture>>

Three lots (each lot is referred to as lot A, lot B, and lot C, respectively) of human epidermal keratinocyte cell sheets differing in cell state from each other were prepared at the time of culturing under the following condition, and these lots each were cultured under the following condition. Culture-supernatant monitoring was made, and correlation between the concentration of an amino acid in the culture supernatant and the cell state was checked. Further, the respective cell states of those cell sheets were determined on the basis of a phase-contrast microscope image obtained during culturing, and a chromatic figure of a tissue section, obtained after the culturing, representing a traditional method for cell sheet evaluation.

<<Experimental Condition>>

An experimental condition in detail is as described hereunder.

For a culture vessel, use was made of an insert structured so as to be divided into two layers, upper and lower, demarcated by a material-permeating membrane. A human epidermal keratinocyte cell and a Keratinocyte Culture Medium (hereinafter referred to as "KCM medium") were put in the upper layer, and the KCM medium was put in the lower layer, whereupon culturing was made on condition that nutrient is imparted to the cell from below as well. The upper layer was disseminated with the human epidermal keratinocyte cell adjusted such that dissemination density was at $2.5 \times 10^4$ cells/cm$^2$, and culturing was made in an incubator at 37° C., and CO$_2$ 5% after dissemination. Replacement of total medium was made in both the upper and lower layers, and culturing was continued for a period of 16 days after the elapse of 4 days, 7 days, 9 days, 11 days, 13 days, 14 days, and 15 days, respectively, after the start of the culturing. With respect to components in the culture supernatant in an old medium recovered at the time of medium replacement, an quantitative analysis by use of the high performance liquid chromatography (HPLC) was executed on 41 species of amino acids (P-Ser, Tau, PEA, Urea, Asp, Thr, Ser, AspNH$_2$, Glu, GluNH$_2$, Sar, a-AAA, Gly, Ala, Cit, a-ABA, Val, Cys, Met, Cysthi, Ile, Leu, Tyr, Phe, b-Ala, b-AiBA, g-ABA, Trp, EOHNH$_2$, NH$_3$, Hylys, Orn, Lys, 1Mehis, His, 3Mehis, Ans, Car, Arg, Hypr, and Pro).

Further, a sample recovered after incubating only a medium not for use in culturing under the same condition was also prepared to be used as a control for verification of a measurement error.

<<Experimental Result>>

An experimental result is as shown in FIG. 2. As shown in FIG. 2, there was observed a difference shown in respect of proliferation, multi-layering, and differentiation, respectively, by the cell lot (the lots A, B, and C, respectively).

The lot A showed that proliferation proceeded up to the confluent in 7 days, and multi-layering showed on the order of 3 layers. With respect to differentiation, the cell underwent differentiation into the respective layers of the basal layer, the stratum spinosum, and the granular layer.

The lot B showed that proliferation proceeded up to the confluent in 9 days, and multi-layering showed on the order of 3 layers. Further, with respect to differentiation, the cell underwent differentiation into the respective layers of the basal layer, and the stratum spinosum.

The respective lots described as above are described in detail. With both the lot A, and the lot B, a cell sheet was formed via the following process.

For a time period up to the confluent after a cell was adhered to a culture surface, the cell underwent proliferation in a single layer, and thereafter, the cells each turned smaller in apparent size, whereupon the cells cobblestone-like in shape came to be observed after the elapse of few days from the confluent, however, no change in a microscope image was observed thereafter even with the elapse of a number of culture days. The lot A differs from the lot B in respect of cell-proliferation rate, and the lot B lags behind the lot A by around 2 days in forming the cell sheet, so that the confluent was reached on the ninth culture day in the case of the lot B, whereas the confluent was reached on the seventh culture day in the case of the lot B.

With the lot C, the number of the cells adhered to the culture surface was found extremely decreased, and the proliferation of the adhered cell was found poor even after the elapse of additional culture days, thereby having failed to reach a point where the cell sheet was formed. Thus, the experimental result of the lot C showed that the proliferation was poor, the multi-layering as well was poor, and the differentiation occurred to the basal layer only, as shown in FIG. 2.

<<41 Species of Amino Acids>>

With respect to the cell culture supernatant of each of these three lots (the lots A, B, and C) and a medium for use as a control, an quantitative analysis was applied to 41 species of amino acids (P-Ser, Tau, PEA, Urea, Asp, Thr, Ser, AspNH$_2$, Glu, GluNH$_2$, Sar, a-AAA, Gly, Ala, Cit, a-ABA, Val, Cys, Met, Cysthi, Ile, Leu, Tyr, Phe, b-Ala, b-AiBA, g-ABA, Trp, EOHNH$_2$, NH$_3$, Hylys, Orn, Lys, 1Mehis, His, 3Mehis, Ans, Car, Arg, Hypr, and Pro), and the result of the quantitative analysis is shown below. A change in the concentration of an amino acid was observed in this quantitative analysis.

The concentration of an amino acid showed a different behavior by the lot, that is, by the cell state. The reason for this is because an amino acid being one of the metabolites of the cell, metabolism thereof undergoes a change accompanying a change in the cell state, so that amino-acid metabolic expenditure as well undergoes a change to be reflected in the concentration of the amino acid in the culture supernatant.

All the samples in common with each other did not detect 21 species of amino acids (P-Ser, Tau, PEA, Urea, AspNH$_2$, Sar, a-AAA, Cit, a-ABA, Cysthi, b-Ala, b-AiBA, g-ABA, EOHNH$_2$, Hylys, 1Mehis, 3Mehis, Ans, Car, Hypr, and Pro), selected from a group consisting of the 41 species of the amino acids, subjected to the analysis.

On the other hand, an amino acid was detected from among the remaining 20 species selected from the group consisting of the 41 species of the amino acids. Accordingly, a review is made on the remaining 20 species of amino acids hereunder. In FIGS. 3A through 3D, there is shown a time-dependent change in the concentration of an amino acid in the culture supernatant with respect to the remaining 20 species of the amino acids.

<<15 Species of Amino Acids>>

Figure 3A:
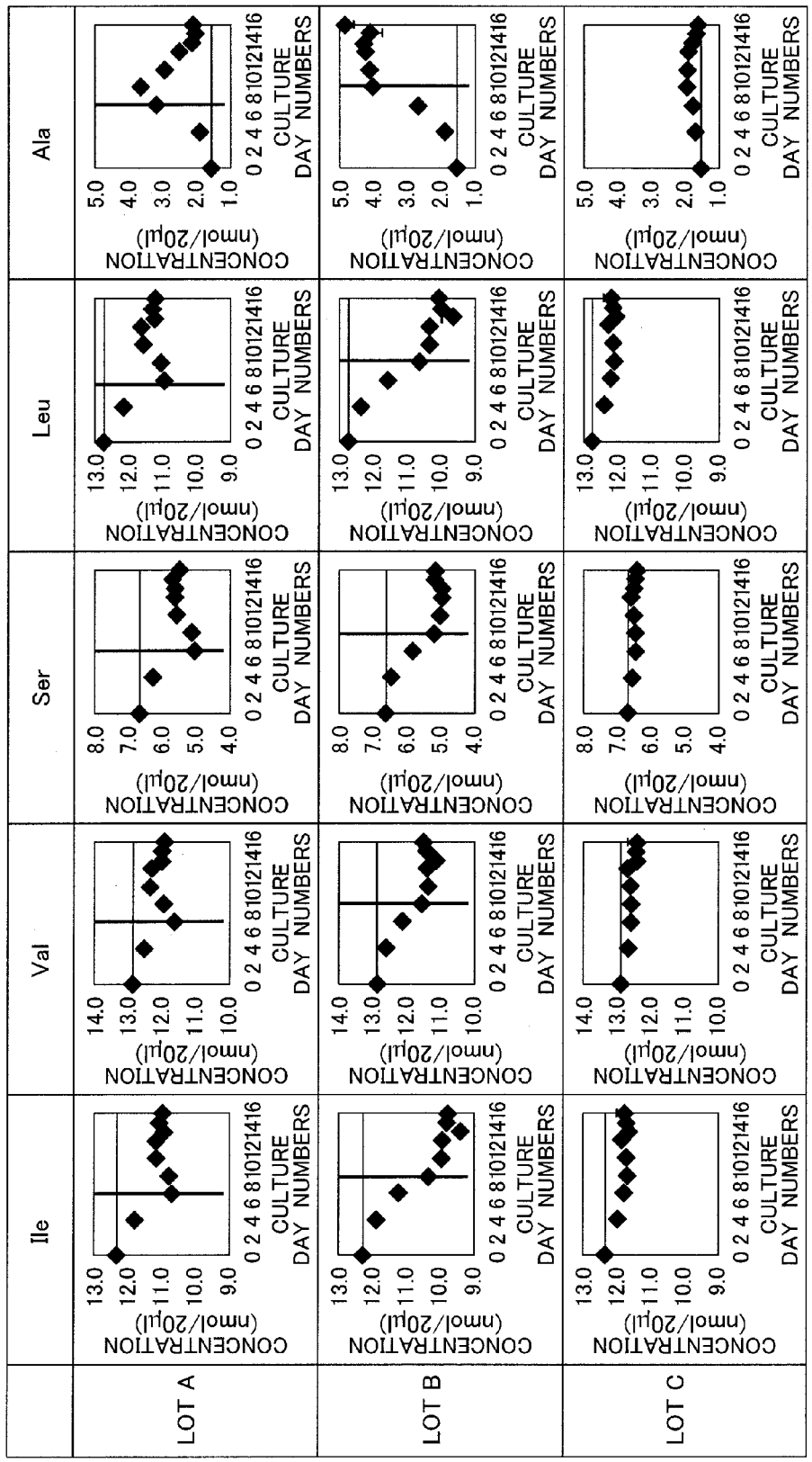
FIG. 3A is a view showing a time-dependent change in the concentration of each amino acid in a culture supernatant, selected from a group consisting of Ile, Val, Ser, Leu, and Ala.
Figure 3B:
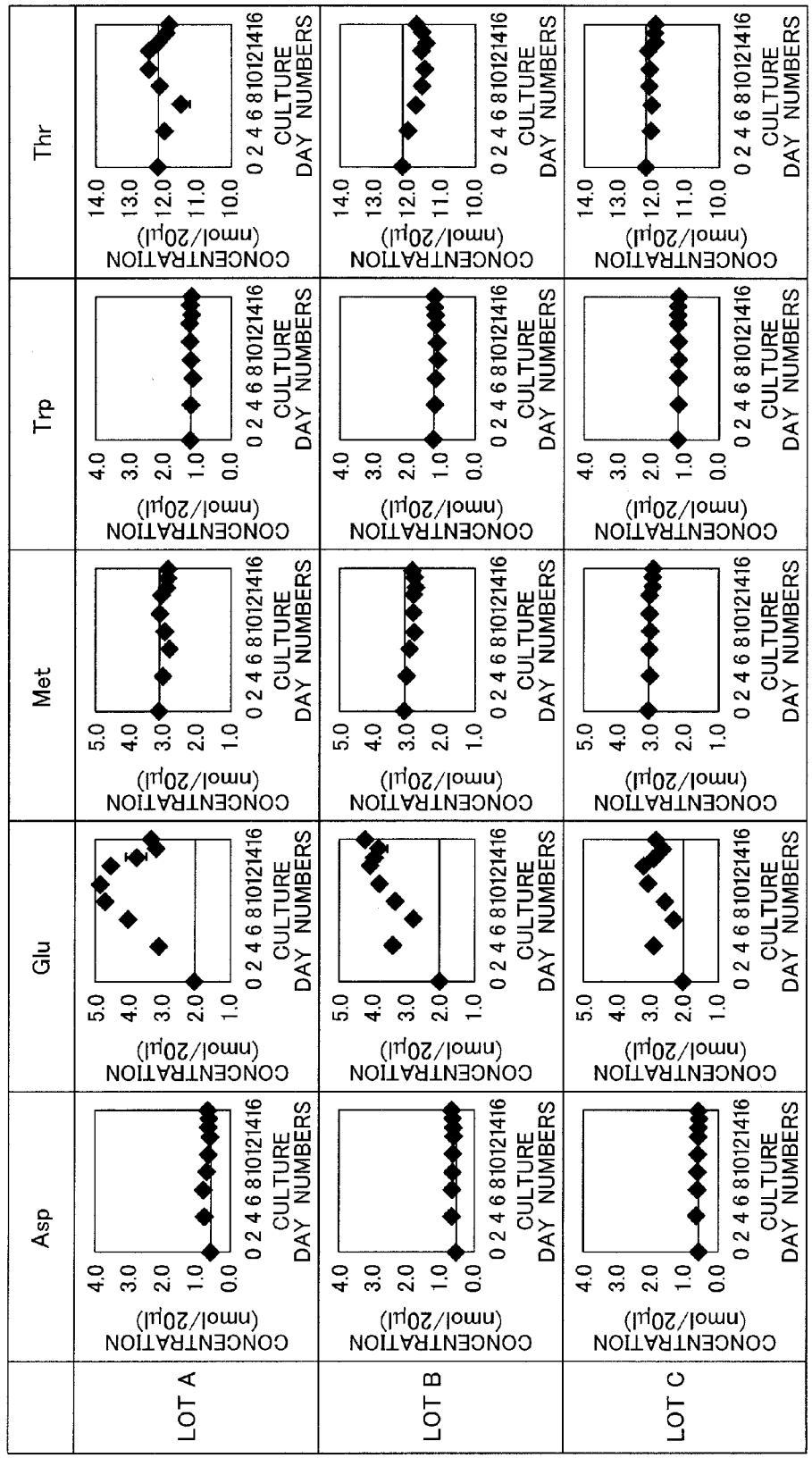
FIG. 3B is a view showing a time-dependent change in the concentration of each amino acid in a culture supernatant, selected from a group consisting of Asp, Glu, Met, Trip, and Thr.
Figure 3C:
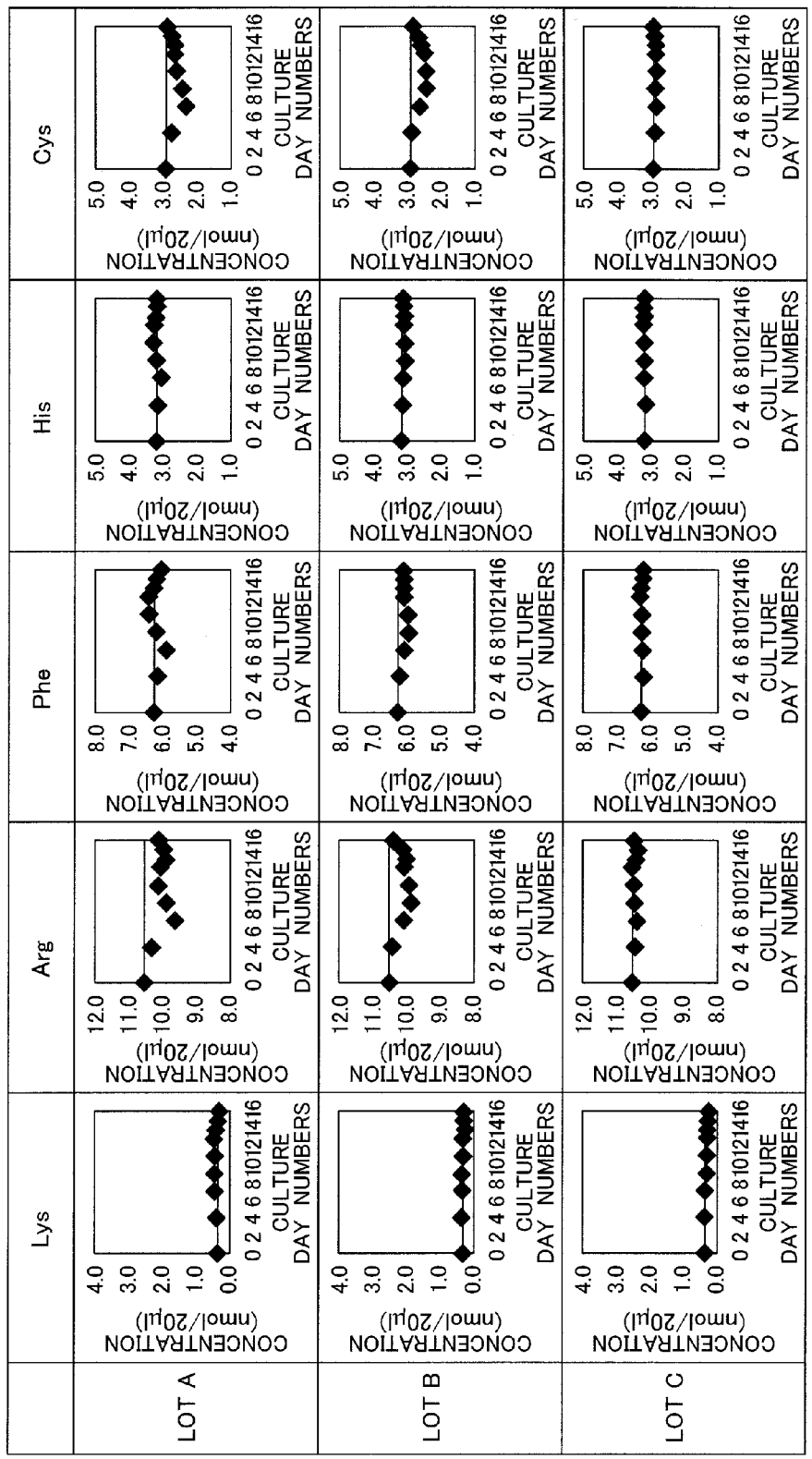
FIG. 3C is a view showing a time-dependent change in the concentration of each amino acid in a culture supernatant, selected from a group consisting of Lys, Arg, Phe, His, and Cys.
Figure 3D:
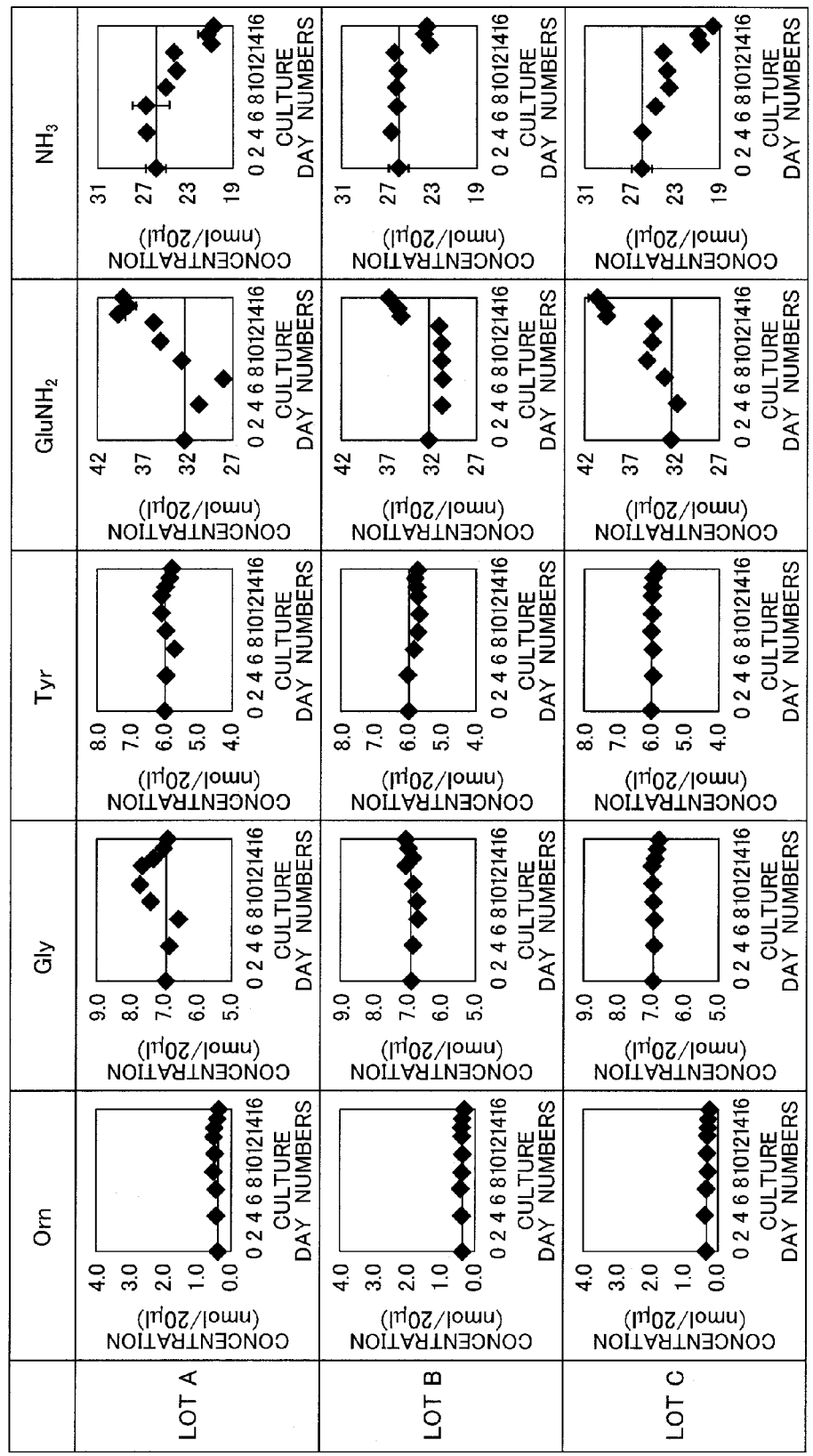
FIG. 3D is a view showing a time-dependent change in the concentration of each amino acid in a culture supernatant, selected from a group consisting of Orn, Gly, Tyr, $GluNH_2$, and $NH_3$.

Now, with respect to 15 species of amino acids (Asp, Thr, Glu, GluNH$_2$, Gly, Cys, Met, Tyr, Phe, Trp, NH$_3$, Orn, Lys, His, and Arg) selected from among the remaining 20 species of the amino acids, a variation in concentration between the concentration before the cell culture and the concentration after the cell culture was not more than the measurement error of a variation found from a sample obtained by incubating only the medium not for use in culturing under the same condition as with case the 15 species of the amino acids to be subsequently recovered, and it was not possible to observe the confluent of the cell (refer to FIGS. 3B through 3D). Accordingly, it was determined that the 15 species of the amino acids were not suited to the analysis of the culture supernatant.

In this connection, the measurement error for every amino acid, used in the determination of a result described as above, is as follows; the measurement error (nmol/20 μl) in analysis of an amino acid in a medium not for use in culturing, measured as the control for the respective amino acids, was Asp: 0.36, Thr: 0.63, Glu: 1.76, GluNH$_2$: 7.32, Gly: 0.26, Cys: 0.16, Met: 0.18, Tyr: 0.29, Phe: 0.40, Trp: 0.07, NH$_3$: 0.59, Orn: 0.09, Lys: 0.62, His: 0.19, and Arg: 0.56, respectively.

On the basis of the result described as above, a review is made on 5 species of the amino acids, the 5 species being the remainder when the 15 species is subtracted from the 20 species.

<<5 Species of Amino Acids>>

The 5 species of the amino acids (Ser, Ala, Val, Ile, Leu) left as a result of screening described as above, each showed a change appropriate for determination on the cell state. Further, the measurement error (nmol/20 μl) in the analysis of an amino acid in the medium was Ser: 0.36, Ala: 0.33, Val: 0.11, Ile: 0.51, and Leu: 0.20, respectively.

In FIGS. 3A through 3D, there is shown hereunder a detailed result on each of the 5 species of the amino acids. FIGS. 3A through 3D each indicate the concentration (nmol/

20 µl) of an amino acid in the culture supernatant on a medium-replacement day (each of $4^{th}$, $7^{th}$, $9^{th}$, $11^{th}$, $13^{th}$, $14^{th}$, and $15^{th}$ days). Herein, a horizontal reference line in the figure indicates an initial value prior to culturing. Accordingly, if a measurement point is present above the reference line, this means that amino acids secreted from the cell are more in amount than amino acids drawn into the cell by metabolism. In contrast, if the measurement point is present below the reference line, this means a reverse phenomenon, that is, the case where the amino acids drawn into the cell is greater in amount than the amino acids secreted from the cell.

Incidentally, since the total medium was replaced with a new one on the medium-replacement day, as described above, it is presumed that the concentration of an amino acid in the culture supernatant reverts to an initial value prior to culturing every time a medium is replaced.

Further, for the concentration of an amino acid, shown in the figure, use is made of a value as converted from the variations for one day because of an irregular time interval between recoveries of the culture supernatant. In the figure showing a culture day number $7^{th}$ day, since the number of successive culture days is three days from the $4^{th}$ day onward, at a point in time, corresponding to the culture day number No. $7^{th}$ day, a variation in the concentration of an amino acid is converted on the basis of a value obtained by dividing the variation in an amino acid against an initial value in the culture supernatant recovered on the $7^{th}$ day by the three successive culture days. Further, since medium replacement is made every day from the culture day No. $13^{th}$ onward, a variation in an amino acid against an initial value in the culture supernatant recovered on that say is used as it is to thereby indicate the concentration of an amino acid.

In FIG. 3A, a vertical reference line indicates a point in time when the cell has reached the confluent. Further, with 4 species among the 5 species of the amino acids, more specifically, in the respective cases of Ile, Val, Ser, and Leu, since the measurement point is below the reference line, the amino acids drawn into the cell exceeds the amino acids secreted from the cell. On the other hand, in the case of only one species among the 5 species of the amino acids, that is, Ala, the measurement point is above the reference line, indicating that the amino acids secreted from the cell exceeds the amino acids drawn into the cell.

Further, with the lot A and the lot B, respectively, an obvious change in the concentration of the amino acid was observed, however, with the lot C, a variation was markedly small as compared with the lots A and B, respectively.

With both the lot A and the lot B, a time-dependent increase in secretion volume of any amino acid selected from the group consisting of Ile, Val, Ser, and Leu was observed in the earlier period of culture, whereas a time-dependent increase in the drawn volume of Ala was observed. However, the trend of a change has partially varied in the later period of culture, onward. Herein, the earlier period of culture indicates a period prior to a point in time when the cell has turned into the confluent, and the later period of culture indicates a period after the point in time when the cell has turned into the confluent.

The following is evident by interpretation of the description given as above.

<<Determination on Cell Proliferation>>

With respect to cell proliferation, it is possible to determine whether or not a cell proliferation process prior to the confluent is satisfactory, on the basis of the concentration of any amino acid selected from among the 5 species of the amino acids (Ile, Val, Ser, Leu, and Ala).

As shown in FIG. 3A, with the lots A and B, respectively, the cell underwent satisfactory proliferation, whereas with the lot C, the cell was poor in proliferation. There is described hereunder a change in the concentration of each of the 5 species of the amino acids, at this point in time.

(1) With the lots A and B, respectively, the concentration of Ile noticeably decreased with time. A value at a point in time, for the confluent, underwent a change of 1.64 (nmol/20 µl) or more, as compared with the initial value. However, with the lot C, a change was smaller and a variation from the initial value during culturing was 0.66 (nmol/20 µl) or less at any point in time.

(2) With the lots A and B, respectively, the concentration of Val noticeably decreased with time. A value at a point in time, for the confluent, underwent a change 1.24 (nmol/20 µl) or more, as compared with the initial value. However, with the lot C, a change was smaller and a variation from the initial value during culturing was 0.33 (nmol/20 µl) or less at any point in time.

(3) With the lots A and B, the concentration of Ser noticeably decreased with time. A value at a point in time, for the confluent, underwent a change 1.48 (nmol/20 µl) or more, as compared with the initial value. However, with the lot C, a change was smaller and a variation from the initial value during culturing was 0.24 (nmol/20 µl) or less at any point in time.

(4) With the lots A and B, the concentration of Leu noticeably decreased with time. A value at a point in time, for the confluent, underwent a change 1.91 (nmol/20 µl) or more, as compared with the initial value. However, with the lot C, a change was smaller and a variation from the initial value during culturing was 1.71 (nmol/20 µl) or less at any point in time.

(5) With the lots A and B, the concentration of Ala noticeably increased with time. A value at a point in time, for the confluent, underwent a change 1.77 (nmol/20 µl) or more, as compared with the initial value. However, with the lot C, a change was smaller and a variation from the initial value during culturing was 0.43 (nmol/20 µl) or less at any point in time.

Accordingly, with respect to cell proliferation, determination on whether or not the cell proliferation is satisfactorily proceeding can be made depending on whether or not a decrease in the concentration of any amino acid selected from the group consisting of Ser, Leu, Val, and Ile, or an increase in the concentration of Ala is not less than a threshold.

Further, with this determination, if respective variations in the concentration of each of the amino acids described as above, at the point in time, for the confluent, and at an initial point in time, are higher than a preset threshold, it is determined that the variation has a significant difference, and the cell proliferation is satisfactory. On the other hand, if the respective variations in the concentration are less than the preset threshold, it is determined that the cell proliferation is unsatisfactory.

For this threshold, use is made of a value pre-selected as an appropriate value for every target against which the cell proliferation is performed, on the basis of experimental data, and so forth.

<<Determination on Cell Multi-Layering>>

With respect to cell multi-layering, it is possible to determine whether or not timing of a multi-layering start and a cell multi-layering process are satisfactory on the basis of the concentration of any amino acid selected from the group consisting of Ile, Val, Ser, Leu, and Ala. With the lots A and B, respectively, the cell satisfactorily underwent multilayering, and with the lot C, multi-layering was poor, however, with the lots A and B, respectively, at this point in time, a change in the concentration of any amino acid, as seen at the time of the cell proliferation, considerably decreased, or was reversed with the confluent as a demarcation. On the other hand, with the lot C, a change in the concentration of an amino acid was hardly observed.

Accordingly, the cell multi-layering can be determined on the basis of whether or not the cell multi-layering starts at timing when a variation in the concentration of any amino acid selected from the group consisting of Ile, Val, Ser, Leu, and Ala considerably decreases, or is reversed, as compared with a variation in the concentration of the amino acid for a time period from the initial state up to before the confluent is reached. If such a variation as above is observed, it is possible to determine that the multi-layering is underway.

<<Determination on Cell Differentiation>>

With respect to cell differentiation, whether or not a cell differentiation process is satisfactory can be determined on the basis of the concentration of Ala. With the lot B, differentiation remained as far as the stratum spinosum, and did not proceed up to the granular layer, whereas with the lot A, differentiation proceeded up to the granular layer. However, with the lot B, a change in the concentration after the confluent was poor, whereas with the lot A, at this point in time, the concentration of Ala decreased with time after the confluent. With the lot B, the concentration of Ala on the $16^{th}$ day was 5.13 (nmol/20 μl) against 2.15 (nmol/20 μl) with the lot A, so that the concentration of Ala of the lot A was lower by 2.98 (nmol/20 μl), Hence, with respect to the differentiation, it is possible to determine whether or not the cell differentiation is satisfactory depending on the trend of a change in the concentration of Ala, and whether or not a decrease in the concentration is not less than a threshold. Further, with respect to each of other amino acids, such as Ile, Val, Ser, and Leu, similar reversal of a change in the concentration thereof was observed after the confluent with the Lot A, not observed in the lot B, although not so noticeable as in the case of Ala, and such reversal can similarly serve as an index of the cell differentiation.

LIST OF REFERENCE SIGNS

1 . . . medium bottle,
2 . . . medium supply flow-path,
3 . . . culture vessel,
4 . . . effluent flow-path,
5 . . . effluent bottle,
6 . . . flow-pat directed for culture-supernatant analysis,
7 . . . analysis column,
8 . . . optical system,
9 . . . detection part
20 . . . temperature • humidity controller,
21 . . . controller,
30 . . . determination part,
31 . . . memory part,
32 . . . effluent flow-path,
33 . . . flow-path directed for culture-supernatant analysis,
100 . . . automated culture unit, and
200 . . . amino acid analysis unit.

The invention claimed is:

1. An autoanalyzer provided with an automated culture unit, and an amino acid analysis unit,
the automated culture unit comprising:
a culture vessel for culturing a human epidermal keratinocyte cell sheet; and
a controller for controlling transportation of a medium introduced in the culture vessel to the amino acid analysis unit, and
the amino acid analysis unit comprising:
a detection part for measuring the respective concentrations of predetermined amino acids contained in the medium transported from the automated culture unit;
a memory part for storing the respective measured concentrations of the amino acids; and
a determination part for determining the cell state of the human epidermal keratinocyte cell sheet on the basis of a change in the concentration of at least one of the amino acids stored in a memory part,
wherein 5 species of amino acids of Ile, Val, Ser, Leu, and Ala are used for the predetermined amino acids, and the change in the concentration of the amino acid is calculated on the basis of the concentration of the amino acid, as measured with time by the detection part over a plurality of times to be stored in the memory part,
wherein in the case where a threshold is preset in the memory part, the determination part calculates a variation in the concentration of an amino acid on the basis of the concentrations of the amino acids, stored in the memory part, and a cell state in which a cell undergoes proliferation in a planar state during culturing on the basis of the variation as calculated is defined as confluent, if the concentration of any amino acid selected from a group consisting of Ile, Val, Ser, and Leu, among the 5 species of the amino acids undergoes a decrease, and a decrease volume of the amino acids is not less than the threshold prior to the confluent, or the concentration of an amino acid of Ala among the group of the 5 species of the amino acids undergoes an increase, an increase volume of the amino acids being not less than the threshold, it is determined that cell proliferation is satisfactorily proceeding.

2. An autoanalyzer provided with an automated culture unit, and an amino acid analysis unit,
the automated culture unit comprising:
a culture vessel for culturing a human epidermal keratinocyte cell sheet and a controller for controlling transportation of a medium introduced in the culture vessel to the amino acid analysis unit, and
the amino acid analysis unit comprising:
a detection part for measuring the respective concentrations of predetermined amino acids contained in the medium transported from the automated culture unit
a memory part for storing the respective measured concentrations of the amino acids; and
a determination part for determining the cell state of the human epidermal keratinocyte cell sheet on the basis of a change in the concentration of at least one of the amino acids stored in a memory part,
wherein 5 species of amino acids of Ile, Val, Ser, Leu, and Ala are used for the predetermined amino acids, and the change in the concentration of the amino acid is calculated on the basis of the concentration of the amino acid, as measured with time by the detection part over a plurality of times to be stored in the memory part,
wherein in the case where the determination part calculates a variation in the concentration of an amino acid on the basis of the concentrations of the amino acids stored in the memory part, and a cell state in which a cell undergoes proliferation in a planar state during culturing on the basis of the variation as calculated is defined as confluent, if a variation in the concentration of any amino acid selected from a group consisting of Ile, Val, Ser, and Leu, among the 5 species of the amino acids, after the confluent, is smaller as compared with the variation in the concentration of an amino acid for a time period from an initial period to the confluent, or a variation in the concentration of an amino acid of Ala among the group of the 5 species of the amino acids, is greater or the same as compared with the variation in the concentration of an amino acid for the time period from the initial period to the confluent, the determination part determines that timing of a multi-layering start and a cell multi-layering process are satisfactorily proceeding.

3. An autoanalyzer provided with an automated culture unit, and an amino acid analysis unit, the automated culture unit comprising:
a culture vessel for culturing a human epidermal keratinocyte cell sheet; and
a controller for controlling transportation of a medium introduced in the culture vessel to the amino acid analysis unit, and the amino acid analysis unit comprising:
a detection part for measuring the respective concentrations of predetermined amino acids contained in the medium transported from the automated culture unit;
a memory part for storing the respective measured concentrations of the amino acids; and
a determination part for determining the cell state of the human epidermal keratinocyte cell sheet on the basis of a change in the concentration of at least one of the amino acids stored in a memory part, wherein 5 species of amino acids of Ile, Val, Ser, Leu, and Ala are used for the predetermined amino acids, and the change in the concentration of the amino acid is calculated on the basis of the concentration of the amino acid, as measured with time by the detection part over a plurality of times to be stored in the memory part, wherein in the case where a threshold is preset in the memory part, the determination part calculates a variation in the concentration of an amino acid on the basis of the respective concentrations of the amino acids, stored in the memory part, and a cell state in which a cell undergoes proliferation in a planar state during culturing on the basis of the variation as calculated is defined as confluent, if the concentration of an amino acid of Ala undergoes an increase prior to the confluent, and the concentration of the amino acid of Ala undergoes a decrease after the confluent, whereupon an increase volume or a decrease volume is not less than the threshold, the determination part determines that differentiation of the human epidermal keratinocyte cell sheet is satisfactorily proceeding.

* * * * *